United States Patent
Draborg et al.

(10) Patent No.: US 9,133,423 B2
(45) Date of Patent: Sep. 15, 2015

(54) SUBTILASE VARIANTS

(75) Inventors: Henriette Draborg, Allerod (DK); Vibeke Skovgaard Nielsen, Bagsvaerd (DK); Stefan Minning, Ballerup (DK)

(73) Assignee: NOVOZYMES A/S, Bagsvaerd (DK)

( * ) Notice: Subject to any disclaimer, the term of this patent is extended or adjusted under 35 U.S.C. 154(b) by 109 days.

(21) Appl. No.: 12/688,057

(22) Filed: Jan. 15, 2010

(65) Prior Publication Data

US 2010/0120091 A1  May 13, 2010

Related U.S. Application Data

(63) Continuation of application No. 11/482,424, filed on Jul. 7, 2006, now abandoned.

(60) Provisional application No. 60/698,254, filed on Jul. 11, 2005.

(30) Foreign Application Priority Data

Jul. 8, 2005 (DK) ................................ 2005 01007

(51) Int. Cl.
  C12N 9/54   (2006.01)
  C11D 3/386  (2006.01)
  C12N 15/52  (2006.01)
  C12N 15/74  (2006.01)

(52) U.S. Cl.
  CPC .............. *C11D 3/38636* (2013.01); *C12N 9/54* (2013.01); *C12N 15/52* (2013.01); *C12N 15/74* (2013.01)

(58) Field of Classification Search
  None
  See application file for complete search history.

(56) References Cited

U.S. PATENT DOCUMENTS

| 5,631,217 | A  | * | 5/1997  | Branner et al. ............... 510/320 |
| 6,271,012 | B1 |   | 8/2001  | Van Eekelen et al. |
| 6,287,841 | B1 | * | 9/2001  | Mulleners et al. ............ 435/221 |
| 6,300,116 | B1 |   | 10/2001 | Von der Osten et al. |
| 6,312,936 | B1 |   | 11/2001 | Poulose et al. |
| 6,376,450 | B1 |   | 4/2002  | Ghosh et al. |
| 6,436,690 | B1 |   | 8/2002  | Brode, III et al. |
| 6,482,628 | B1 |   | 11/2002 | Poulose et al. |
| 6,569,663 | B1 |   | 5/2003  | Rubingh et al. |
| 6,599,730 | B1 |   | 7/2003  | Brode, III et al. |
| 6,632,646 | B1 | * | 10/2003 | Aaslyng et al. ............... 435/220 |
| 2002/0128167 | A1 | * | 9/2002  | Ghosh et al. .................. 510/392 |
| 2004/0147008 | A1 |   | 7/2004  | Draborg et al. |
| 2004/0197894 | A1 |   | 10/2004 | Fano et al. |
| 2005/0181446 | A1 | * | 8/2005  | Roggen et al. ................. 435/7.1 |
| 2006/0228791 | A1 | * | 10/2006 | Roggen et al. ................ 435/222 |
| 2011/0092408 | A1 | * | 4/2011  | Draborg et al. .............. 510/226 |
| 2012/0172280 | A1 | * | 7/2012  | Knotzel et al. ................ 510/392 |
| 2012/0252106 | A1 | * | 10/2012 | Knotzel et al. ................ 435/264 |

FOREIGN PATENT DOCUMENTS

| WO | WO 99/20726    | 4/1999  |
| WO | WO 99/27082    | 6/1999  |
| WO | WO 01/44452    | 6/2001  |
| WO | WO 01/083559   | 11/2001 |
| WO | WO 02/16547    | 2/2002  |
| WO | 2004/041979 A2 | 5/2004  |

* cited by examiner

*Primary Examiner* — Manjunath Rao
*Assistant Examiner* — William W Moore
(74) *Attorney, Agent, or Firm* — Kristin J. McNamara

(57) ABSTRACT

The present invention relates to novel subtilase variants exhibiting improvements relative to the parent subtilase in one or more properties including: wash performance, thermal stability, storage stability or catalytic activity. The variants of the invention are suitable for use in e.g., cleaning or detergent compositions, such as laundry detergent compositions and dish wash compositions, including automatic dish wash compositions.

9 Claims, 1 Drawing Sheet

```
No:     1          10         20         30         40         50
a)      AQSVPYGVSQIKAPALHSQGYTGSNVKVAVIDSGIDSSHPDLKVAGGASM
b)      AQSVPWGISRVQAPAAHNRGLTGSGVKVAVLDTGI*STHPDLNIRGGASF

No:                60         70         80         90        100
a)      VPSETNPFQDNNSHGTHVAGTVAALNNSIGVLGVAPSASLYAVKVLGADG
b)      VPGEPST*QDGNGHGTHVAGTIAALNNSIGVLGVAPSAELYAVKVLGASG

No:               110        120        130        140        150
a)      SGQYSWIINGIEWAIANNMDVINMSLGGPSGSAALKAAVDKAVASGVVVV
b)      SGSVSSIAQGLEWAGNNGMHVANLSLGSPSPSATLEQAVNSATSRGVLVV

No:               160        170        180        190        200
a)      AAAGNEGTSGSSSTVGYPGKYPSVIAVGAVDSSNQRASFSSVGPELDVMA
b)      AASGNSG*AGS***ISYPARYANAMAVGATDQNNNRASFSQYGAGLDIVA

No:               210        220        230        240        250
a)      PGVSIQSTLPGNKYGAYNGTSMASPHVAGAAALILSKHPNWTNTQVRSSL
b)      PGVNVQSTYPGSTYASLNGTSMATPHVAGAAALVKQKNPSWSNVQIRNHL

No:               260       270   275
a)      ENTTTKLGDSFYYGKGLINVQAAAQ
b)      KNTATSLGSTNLYGSGLVNAEAATR
```

SUBTILASE VARIANTS

CROSS-REFERENCE TO RELATED APPLICATIONS

This application is a continuation of U.S. application Ser. No. 11/482,424 filed on Jul. 7, 2006 (abandoned) and claims priority or the benefit under 35 U.S.C. 119 of Danish Application no. PA 2005 01007 filed Jul. 8, 2005 and U.S. Provisional Application No. 60/698,254 filed Jul. 11, 2005, the contents of which are fully incorporated herein by reference.

REFERENCE TO A SEQUENCE LISTING

This application contains a Sequence Listing in computer readable form. The computer readable form is incorporated herein by reference.

FIELD OF THE INVENTION

The present invention relates to novel subtilase variants exhibiting alterations relative to the parent subtilase in one or more properties including: wash performance, thermal stability, storage stability and catalytic activity. The variants of the invention are suitable for use in e.g., cleaning or detergent compositions, such as laundry detergent compositions and dish wash compositions, including automatic dish wash compositions. The present invention also relates to isolated DNA sequences encoding the variants, expression vectors, host cells, and methods for producing and using the variants of the invention. Further, the present invention relates to cleaning and detergent compositions comprising the variants of the invention.

BACKGROUND OF THE INVENTION

In the detergent industry enzymes have for more than 30 years been implemented in washing formulations. Enzymes used in such formulations comprise proteases, lipases, amylases, cellulases, as well as other enzymes, or mixtures thereof. Commercially the most important enzymes are proteases.

An increasing number of commercially used proteases are protein engineered variants or naturally occurring wild type proteases, e.g., RELASE®, ALCALASE®, SAVINASE®, PRIMASE®, EVERLASE®, ESPERASE®, OVOZYME®, CORONOASE, POLARZYME® and KANNASE® (Novozymes A/S), MAXATASE™, MAXACAL™, MAXAPE™, PROPERASE™, PURAFECT™, PURAFECT OXP™, FN2™, FN3™, FN4™ and PURAFECT PRIME™ (Genencor International, Inc.), BLAP X and BLAP S (Henkel). Further, a number of protease variants are described in the art. A list of prior art protease variants is given in WO 99/27082.

However, even though a large number of useful protease variants have been described, there is still a need for new improved proteases or protease variants for a number of industrial uses such as laundry or hard surface cleaning. Therefore, an object of the present invention is to provide improved subtilase variants for such purposes.

SUMMARY OF THE INVENTION

Thus, in a first aspect the present invention relates to a subtilase variant comprising one or more of the modifications listed in Table 1.

TABLE 1

Modifications in subtilase variants.

T143K, Y167A, R170S, A194P
Y167A, R170S, A194P, K251R
Y167A, R170S, A194P, S265K
Y167A, R170S, A194P, V244R
S141E, Y167A, R170S, A194P
Y167A, R170S, M175I
Y167A, R170S, A172T
Y167A, R170S, A174V, M175F
Y167A, R170S, A172V, A174V
Y167A, R170S, A172E
Y167A, R170S, M175L
Y167A, R170S, A174T
Y167A, R170S, A174T, M175L
G53C, G61E
A98S, S99D, G100S
S9R, T22A, V68A, S99A, *99Ad
S9R, P14H, R19L, N62D
G61P, *99aS
N43S, N62D
*96aG, P131S, V203A, A228T
N62D, A232C, Q236L, Q245N
*96aA, A98T, R247K
S99D, S101R, S103A, V104I, G160S, A194P, L217D
*61aD
N62D, S106A
V68A, S106M, N184D
S9R, A15T, *97aV, H120N
A15M, A16P, *99aD
*99aE, G160S, S163T, G195S, G211S, K237R, G258A, T260L
G23S, *99aD, A194P, S242T, Q245R
G100S, N173D
Y167A, R170S, A172E
A98T, Q137L, Y167A, R170S, M175L
*98aA, S99D
S99A, *99aD, V203A
N62D, K237R
V11M, N76D, L126F, K251R
S9F, A15L, A16P, T22I, *98aA, S99D, R170H
*96aA, *130aG, P131H
E54D, N62D
*98aA, *98bS, S99G, S101T
S9R, A15T, V68A, I79T, G102S, P131H, Q137H
*100aA, *100bG, *100cS, *100dG
V68A, L111I
*98aA, R170H, Q245R
I35V, N62D, N183D, T224S
*97aG, P131S, V203A, A228T
S9R, R10K, P14Q, T22A, Y167A, R170S
S9R, *22aL, S57A, G61E, *98aA, V139L, N173S
P14T, N18K, Y167A, R170S
S9R, Q12E, P14Q, K27R, Y167A, R170S
N62D, R170L
N62D, R170S, Q245R
Y167A, R170S, A194P, K251R, S265K
P14T, N18K, Y167A, R170S, A194P
N62D, A151G, K237R
N62D, A151G, Q245R
N62D, A151G, K237R, Q245R
S103A, V104I, G159S, A232V, Q236H, Q245R
S9R, A15T, T22A, V139L
S9R, A15T, G61E, A85T, E89Q, P239L, Q245C
S9R, A15T, V68A, H120N, Q245R
N248R
S9R, A15T, *22AI, V139L, N204D, Q245L
N218S
S9R, A15T, V68A, Q245R, N252K
S9R, A15T, V68A, Q245R, H120N
V68A, S106A, H120N
V68A, S106A, N252K
A15T, V68A, S99G, Q245R, N261D
S9R, V68A, S99G, Q245R, N261D
V68A, S99G, Q245R, N261D
S9R, A15T, V68A, S99G, N261D
S9R, A15T, V68A, Q245R, N261D
S9R, A15T, *22aL, V139L, S163G, N204D, Q245L
Q245R, N252H
S9R, *22aL, G61E, *97aA, M119I, Q137H, N173S
V68A, S106A, T213A

TABLE 1-continued

Modifications in subtilase variants.

S9R, A15T, V68A, H120N, P131S, Q137H, Q245M
S9R, A15T, V68A, I72F, S99G, Q245R, N261D
S9R, A15T, V68A, S99D, Q245R, N261D
S9R, A15T, V68A, S99G, A194P, Q245R, N261D
S9R, A15T, V68A, N76I, S99G, Q245R, N261D
S9R, A15T, V68A, S99G, A228V, Q245R, N261D

The variants listed in Table 1 exhibit protease activity. Each position corresponds to a position of the amino acid sequence of subtilisin BPN' set forth in FIG. 1 and SEQ ID NO: 1.

In a second aspect the present invention relates to an isolated polynucleotide encoding a subtilase variant of the invention.

In a third aspect the present invention relates to an expression vector comprising the isolated polynucleotide of the invention.

In a fourth aspect the present invention relates to a microbial host cell transformed with the expression vector of the invention.

In a fifth aspect the present invention relates to a method for producing a subtilase variant according to the invention, comprising culturing a host according to the invention under conditions conducive to the expression and secretion of the variant, and recovering the variant.

In a sixth aspect the present invention relates to a cleaning or detergent composition, preferably a laundry or dish wash composition, comprising the variant of the invention. Concerning alignment and numbering, reference is made to FIG. 1 which shows an alignment between subtilisin BPN' (a) (BASBPN) and subtilisin 309 (b) (BLSAVI). This alignment is in this patent application used as a reference for numbering the residues.

DEFINITIONS

Prior to discussing this invention in further detail, the following terms and conventions will first be defined. For a detailed description of the nomenclature of amino acids and nucleic acids, we refer to WO 00/71691 beginning at page 5, which is herein incorporated by reference.

Nomenclature and Conventions for Designation of Variants

In describing the various subtilase enzyme variants produced or contemplated according to the invention, the following nomenclatures and conventions have been adapted for ease of reference: A frame of reference is first defined by aligning the isolated or parent enzyme with subtilisin BPN' (BASBPN).

The alignment can be obtained by the GAP routine of the GCG package version 9.1 to number the variants using the following parameters: gap creation penalty=8 and gap extension penalty=8 and all other parameters kept at their default values.

Another method is to use known recognized alignments between subtilases, such as the alignment indicated in WO 91/00345. In most cases the differences will not be of any importance.

Thereby a number of deletions and insertions will be defined in relation to BASBPN (SEQ ID NO: 1). In FIG. 1, subtilisin 309 (SEQ ID NO: 2) has 6 deletions in positions 36, 58, 158, 162, 163, and 164 in comparison to BASBPN. These deletions are in FIG. 1 indicated by asterixes (*). For a detailed description of the nomenclature of modifications introduced in a polypeptide by genetic manipulation we refer to WO 00/71691 page 7-12, which is herein incorporated by reference.

Proteases Enzymes cleaving the amide linkages in protein substrates are classified as proteases, or (interchangeably) peptidases (see Walsh, 1979, *Enzymatic Reaction Mechanisms*. W.H. Freeman and Company, San Francisco, Chapter 3).

Numbering of amino acid positions/residues If nothing else is mentioned the amino acid numbering used herein correspond to that of the subtilase BPN' (BASBPN) sequence. For further description of the BPN' sequence, see FIG. 1, SEQ ID NO: 1 or Siezen et al., 1991, *Protein Engng.* 4:719-737.

Serine proteases A serine protease is an enzyme which catalyzes the hydrolysis of peptide bonds, and in which there is an essential serine residue at the active site (White, Handler and Smith, 1973 *"Principles of Biochemistry,"* Fifth Edition, McGraw-Hill Book Company, NY, pp. 271-272). The bacterial serine proteases have molecular weights in the 20,000 to 45,000 Dalton range. They are inhibited by diisopropylfluorophosphate. They hydrolyze simple terminal esters and are similar in activity to eukaryotic chymotrypsin, also a serine protease. A more narrow term, alkaline protease, covering a sub-group, reflects the high pH optimum of some of the serine proteases, from pH 9.0 to 11.0 (for review, see Priest, 1977, *Bacteriological Rev.* 41:711-753).

Subtilases A sub-group of the serine proteases tentatively designated subtilases has been proposed by Siezen et al., 1991, *Protein Engng.* 4:719-737 and Siezen et al., 1997, *Protein Science* 6:501-523. They are defined by homology analysis of more than 170 amino acid sequences of serine proteases previously referred to as subtilisin-like proteases. A subtilisin was previously often defined as a serine protease produced by Gram-positive bacteria or fungi, and according to Siezen et al. now is a subgroup of the subtilases. A wide variety of subtilases have been identified, and the amino acid sequence of a number of subtilases has been determined. For a more detailed description of such subtilases and their amino acid sequences reference is made to Siezen et al. (1997).

One subgroup of the subtilases, I-S1 or "true" subtilisins, comprises the "classical" subtilisins, such as subtilisin 168 (BSS168), subtilisin BPN', subtilisin Carlsberg (ALCALASE®, Novozymes A/S), and subtilisin DY (BSSDY).

A further subgroup of the subtilases, I-S2 or high alkaline subtilisins, is recognized by Siezen et al. (supra). Sub-group I-S2 proteases are described as highly alkaline subtilisins and comprises enzymes such as subtilisin PB92 (BAALKP) (MAXACAL®, Genencor International Inc.), subtilisin 309 (SAVINASE®, Novozymes A/S), subtilisin 147 (BLS147) (ESPERASE®, Novozymes A/S), and alkaline elastase YaB (BSEYAB).

"SAVINASE®". SAVINASE® which is marketed by Novozymes A/S is subtilisin 309 from *B. lentus* and differs from BAALKP only in one position (N87S). SAVINASE® has the amino acid sequence designated b) in FIG. 1 and in SEQ ID NO: 2.

Parent subtilase. The term "parent subtilase" describes a subtilase defined according to Siezen et al. (1991 and 1997). For further details see description of "Subtilases" above. A parent subtilase may also be a subtilase isolated from a natural source, wherein subsequent modifications have been made while retaining the characteristic of a subtilase. Furthermore, a parent subtilase may be a subtilase which has been prepared by the DNA shuffling technique, such as described by J. E. Ness et al., 1999, *Nature Biotechnology* 17:893-896. Alternatively the term "parent subtilase" may be termed "wild type subtilase".

Modification(s) of a subtilase variant. The term "modification(s)" used herein is defined to include chemical modification of a subtilase as well as genetic manipulation of the DNA encoding a subtilase. The modification(s) can be replacement(s) of the amino acid side chain(s), substitution(s), deletion(s) and/or insertions in or at the amino acid(s) of interest.

Subtilase variant. In the context of this invention, the term subtilase variant or mutated subtilase means a subtilase that has been produced by an organism which is expressing a mutant gene derived from a parent microorganism which possessed an original or parent gene and which produced a corresponding parent enzyme, the parent gene having been mutated in order to produce the mutant gene from which said mutated subtilase protease is produced when expressed in a suitable host.

Homologous subtilase sequences. The homology between two amino acid sequences is in this context described by the parameter "identity". In order to determine the degree of identity between two subtilases the GAP routine of the GCG package version 9.1 can be applied (infra) using the same settings. The output from the routine is besides the amino acid alignment the calculation of the "Percent Identity" between the two sequences. Based on this description it is routine for a person skilled in the art to identify suitable homologous subtilases, which can be modified according to the invention.

Isolated polynucleotide. The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, Nature 316:774-78, 1985). The term "an isolated polynucleotide" may alternatively be termed "a cloned polynucleotide".

Isolated protein. When applied to a protein, the term "isolated" indicates that the protein has been removed from its native environment. In a preferred form, the isolated protein is substantially free of other proteins, particularly other homologous proteins (i.e., "homologous impurities" (see below)). An isolated protein is more than 10% pure, preferably more than 20% pure, more preferably more than 30% pure, as determined by SDS-PAGE. Further it is preferred to provide the protein in a highly purified form, i.e., more than 40% pure, more than 60% pure, more than 80% pure, more preferably more than 95% pure, and most preferably more than 99% pure, as determined by SDS-PAGE. The term "isolated protein" may alternatively be termed "purified protein".

Homologous impurities. The term "homologous impurities" means any impurity (e.g., another polypeptide than the subtilase of the invention), which originate from the homologous cell where the subtilase of the invention is originally obtained from.

Obtained from. The term "obtained from" as used herein in connection with a specific microbial source, means that the polynucleotide and/or subtilase produced by the specific source, or by a cell in which a gene from the source has been inserted.

Substrate. The term "substrate" used in connection with a substrate for a protease should be interpreted in its broadest form as comprising a compound containing at least one peptide (amide) bond susceptible to hydrolysis by a subtilisin protease.

Product. The term "product" used in connection with a product derived from a protease enzymatic reaction should, in the context of the present invention, be interpreted to include the products of a hydrolysis reaction involving a subtilase protease. A product may be the substrate in a subsequent hydrolysis reaction.

Wash Performance. In the present context the term "wash performance" is used as an enzyme's ability to remove proteinaceous or organic stains present on the object to be cleaned during e.g., wash or hard surface cleaning. See also the wash performance test in Example 3 herein.

BRIEF DESCRIPTION OF THE DRAWING

FIG. 1 shows an alignment between subtilisin BPN' (a) and SAVINASE® (b) using the GAP routine mentioned above.

DETAILED DESCRIPTION OF THE INVENTION

The present invention relates to novel subtilase variants exhibiting alterations relative to the parent subtilase in one or more properties including: Wash performance, thermal stability, storage stability or catalytic activity. Variants which are contemplated as being part of the invention are such variants where, when compared to the wild-type subtilase, one or more amino acid residues have been modified by substitution, deletion or insertion. The variants of the present invention comprise one or more of those modifications listed in Table 1.

The variants listed in Table 1 exhibit protease activity, and each position corresponds to a position of the amino acid sequence of subtilisin BPN' showed in FIG. 1 and SEQ ID NO: 1.

A subtilase variant of the first aspect of the invention may be a parent or wild-type subtilase identified and isolated from nature. Such a parent wild-type subtilase may be specifically screened for by standard techniques known in the art.

One preferred way of doing this may be by specifically PCR amplify conserved DNA regions of interest from subtilases from numerous different microorganism, preferably different Bacillus strains.

Subtilases are a group of conserved enzymes, in the sense that their DNA and amino acid sequences are homologous. Accordingly it is possible to construct relatively specific primers flanking the polynucleotide sequences of interest.

Using such PCR primers to amplify DNA from a number of different microorganisms, preferably different Bacillus strains, followed by DNA sequencing of said amplified PCR fragments, it will be possible to identify strains which produce subtilase variants of the invention. Having identified the strain and a partial DNA sequence of such a subtilase of interest, it is routine work for a person skilled in the art to complete cloning, expression and purification of such a subtilase. However, it is envisaged that a subtilase variant of the invention is predominantly a variant of a parent subtilase.

A subtilase variant suitable for the uses described herein may be constructed by standard techniques known in the art such as by site-directed/random mutagenesis or by DNA shuffling of different subtilase sequences. See the "Material and Methods" section and Example 1 herein for further details.

As will be acknowledged by the skilled person, the variants described herein may comprise one or more additional modifications, in particular one or more additional substitutions or insertions. Moreover, the variants described herein may encompass mutation at more than just one position. For example the variant according to the invention may contain mutations at one position, two positions, three positions or more than three positions, such as four to eight positions. It is preferred that the parent subtilase belongs to the subgroups I-S1 or I-S2, especially subgroup I-S2, both for enzymes from nature or from the artificial creation of diversity, and for designing and producing variants from a parent subtilase.

In relation to variants from subgroup I-S1, it is preferred to select a parent subtilase from the group consisting of BSS168 (BSSAS, BSAPRJ, BSAPRN, BMSAMP), BASBPN, BSSDY, BLSCAR (BLKERA, BLSCA1, BLSCA2, BLSCA3), BSSPRC, and BSSPRD, or functional variants thereof having retained the characteristic of sub-group I-S1.

In relation to variants from subgroup I-S2 it is preferred to select a parent subtilase from the group consisting of BSAPRQ, BLS147 (BSAPRM, BAH101), BLSAVI (BSKSMK, BAALKP, BLSUBL), BYSYAB, BAPB92, TVTHER, and BSAPRS, or functional variants thereof having retained the characteristic of sub-group I-S2. In particular, the parent subtilase is BLSAVI (SAVINASE®, Novozymes A/S), and a preferred subtilase variant of the invention is accordingly a variant of SAVINASE®.

The present invention also encompasses any of the above mentioned subtilase variants in combination with any other modification to the amino acid sequence thereof. Especially combinations with other modifications known in the art to provide improved properties to the enzyme are envisaged. The art describes a number of subtilase variants with different improved properties and a number of those are mentioned in the "Background of the invention" section. Those references are disclosed here as references to identify a subtilase variant, which advantageously can be combined with a subtilase variant described herein. Such combinations comprise the positions: 222 (improves oxidation stability), 218 (improves thermal stability), substitutions in the $Ca^{2+}$-binding sites stabilizing the enzyme, e.g., position 76, and many other apparent from the prior art.

In further embodiments a subtilase variant described herein may advantageously be combined with one or more modification(s) in any of the positions: 27, 36, 56, 76, 87, 95, 96, 97, 98, 99, 100, 101, 102, 103, 104, 120, 123, 159, 167, 170, 206, 218, 222, 224, 232, 235, 236, 245, 248, 252 and 274.

Specifically, the following BLSAVI, BLSUBL, BSKSMK, and BAALKP modifications are considered appropriate for combination:
K27R, *36D, S56P, N62D, V68A, N76D, S87N, G97N, S99SE, S101G, S101R, S103A, V104A, V104I, V104N, V104Y, S106A, H120D, H120N, N123S, G159D, Y167A, R170S, R170L, A194P, N204D, V205I, Q206E, L217D, N218S, N218D, M222S, M222A, T224S, A232V, K235L, Q236H, Q245R, N248D, N252K and T274A.

Furthermore variants comprising any of the modifications S101G+V104N, S87N+S101G+V104N, K27R+V104Y+N123S+T274A, N76D+S103A+V104I, S99D+S101R+S103A+V104I+G160S, S3T+V4I+S99D+S101R+S103A+V104I+G160S+V199M+V205I+L217D, S3T+V4I+S99D+S101R+S103A+V104I+G160S+A194P+V199M+V205I+L217D, S3T+V4I+S99D+S101R+S103A+V104I+G160S+V205I or N76D+V104A, or other combinations of the modifications K27R, *36D, S56P, N62D, V68A, N76D, S87N, G97N, S99SE, S101G, S103A, V104A, V104I, V104N, V104Y, S106A, H120D, H120N, N123S, G159D, Y167A, R170S, R170L, A194P, N204D, V205I, Q206E, L217D, N218S, N218D, M222A, M222S, T224S, A232V, K235L, Q236H, Q245R, N248D, N252K and T274A in combination with any one or more of the modification(s) mentioned above exhibit improved properties. A particular interesting variant is a variant, which, in addition to a modification according to the invention, contains the following substitutions:
S101G+S103A+V104I+G159D+A232V+Q236H+ Q245R+ N248D+N252K.

Moreover, subtilase variants of the main aspect(s) of the invention are preferably combined with one or more modification(s) in any of the positions 129, 131 and 194, preferably as 129K, 131H and 194P modifications, and most preferably as P129K, P131H and A194P modifications. Any of those modification(s) are expected to provide a higher expression level of the subtilase variant in the production thereof.

The wash performance of a selected variant of the invention may be tested in the wash performance test disclosed in Example 3 herein. The wash performance test may be employed to assess the ability of a variant, when incorporated in a standard or commercial detergent composition, to remove proteinaceous stains from a standard textile as compared to a reference system, namely the parent subtilase or a similar subtilase exhibiting an even better wash performance (incorporated in the same detergent system and tested under identical conditions). The enzyme variants of the present application were tested using the Automatic Mechanical Stress Assay (AMSA). With the AMSA test the wash performance of a large quantity of small volume enzyme-detergent solutions can be examined rapidly. Using this test, the wash performance of a selected variant can be initially investigated, the rationale being that if a selected variant does not show a significant improvement in the test compared to the parent subtilase, it is normally not necessary to carry out further test experiments.

Therefore, variants which are particularly interesting for the purposes described herein, are such variants which, when tested in a commercial detergent composition such as a US type detergent, an Asian type, a European type or a Latin American type detergent as described in the wash performance test (Example 3), shows an improved wash performance as compared to the parent subtilase tested under identical conditions.

The improvement in the wash performance may be quantified by calculating the so-called intensity value (Int) defined in Example 3, herein.

Evidently, it is preferred that the variant of the invention fulfils the above criteria on at least the stated lowest level, more preferably at the stated highest level.

Producing a Subtilase Variant

Many methods for cloning a subtilase and for introducing substitutions, deletions or insertions into genes (e.g., subtilase genes) are well known in the art.

In general standard procedures for cloning of genes and introducing mutations (random and/or site directed) into said genes may be used in order to obtain a subtilase variant of the invention. For further description of suitable techniques reference is made to Example 1 herein (vide infra) and (Sambrook et al., 1989, Molecular Cloning: A Laboratory Manual, Cold Spring Harbor lab., Cold Spring Harbor, N.Y.; Ausubel et al. (eds.) "Current protocols in Molecular Biology". John Wiley and Sons, 1995; Harwood and Cutting (eds.) "Molecular Biological Methods for *Bacillus*". John Wiley and Sons, 1990), and WO 96/34946.

Further, a subtilase variant may be constructed by standard techniques for artificial creation of diversity, such as by DNA shuffling of different subtilase genes (WO 95/22625; Stemmer, 1994, *Nature* 370:389-91). DNA shuffling of, e.g., the gene encoding SAVINASE® with one or more partial subtilase sequences identified in nature, will after subsequent screening for improved wash performance variants, provide subtilase variants suitable for the purposes described herein.

Expression Vectors

A recombinant expression vector comprising a DNA construct encoding the enzyme of the invention may be any vector that may conveniently be subjected to recombinant DNA procedures. The choice of vector will often depend on the host cell into which it is to be introduced. Thus, the vector may be an autonomously replicating vector, i.e., a vector that exists as an extra-chromosomal entity, the replication of which is independent of chromosomal replication, e.g., a plasmid.

Alternatively, the vector may be one that on introduction into a host cell is integrated into the host cell genome in part or in its entirety and replicated together with the chromosome(s) into which it has been integrated.

The vector is preferably an expression vector in which the DNA sequence encoding the enzyme of the invention is operably linked to additional segments required for transcription of the DNA. In general, the expression vector is derived from plasmid or viral DNA, or may contain elements of both. The term, "operably linked" indicates that the segments are arranged so that they function in concert for their intended purposes, e.g., transcription initiates in a promoter and proceeds through the DNA sequence coding for the enzyme.

The promoter may be any DNA sequence that shows transcriptional activity in the host cell of choice and may be derived from genes encoding proteins either homologous or heterologous to the host cell.

Examples of suitable promoters for use in bacterial host cells include the promoter of the *Bacillus stearothermophilus* maltogenic amylase gene, the *Bacillus licheniformis* alpha-amylase gene, the *Bacillus amyloliquefaciens* alpha-amylase gene, the *Bacillus subtilis* alkaline protease gene, or the *Bacillus pumilus* xylosidase gene, or the phage Lambda $P_R$ or $P_L$ promoters or the *E. coli* lac, trp or tac promoters. The DNA sequence encoding the enzyme of the invention may also, if necessary, be operably connected to a suitable terminator.

The recombinant vector of the invention may further comprise a DNA sequence enabling the vector to replicate in the host cell in question. The vector may also comprise a selectable marker, e.g., a gene the product of which complements a defect in the host cell, or a gene encoding resistance to e.g., antibiotics like kanamycin, chloramphenicol, erythromycin, tetracycline, spectinomycine, or the like, or resistance to heavy metals or herbicides.

To direct an enzyme of the present invention into the secretory pathway of the host cells, a secretory signal sequence (also known as a leader sequence, prepro sequence or pre sequence) may be provided in the recombinant vector. The secretory signal sequence is joined to the DNA sequence encoding the enzyme in the correct reading frame. Secretory signal sequences are commonly positioned 5' to the DNA sequence encoding the enzyme. The secretory signal sequence may be that normally associated with the enzyme or may be from a gene encoding another secreted protein.

The procedures used to ligate the DNA sequences coding for the present enzyme, the promoter and optionally the terminator and/or secretory signal sequence, respectively, or to assemble these sequences by suitable PCR amplification schemes, and to insert them into suitable vectors containing the information necessary for replication or integration, are well known to persons skilled in the art (cf., for instance, Sambrook et al., op. cit.).

Host Cell

The DNA sequence encoding the present enzyme introduced into the host cell may be either homologous or heterologous to the host in question. If homologous to the host cell, i.e., produced by the host cell in nature, it will typically be operably connected to another promoter sequence or, if applicable, another secretory signal sequence and/or terminator sequence than in its natural environment. The term "homologous" is intended to include a DNA sequence encoding an enzyme native to the host organism in question. The term "heterologous" is intended to include a DNA sequence not expressed by the host cell in nature. Thus, the DNA sequence may be from another organism, or it may be a synthetic sequence.

The host cell into which the DNA construct or the recombinant vector of the invention is introduced may be any cell that is capable of producing the present enzyme and includes bacteria, yeast, fungi and higher eukaryotic cells including plants.

Examples of bacterial host cells which, on cultivation, are capable of producing the enzyme of the invention are gram-positive bacteria such as strains of *Bacillus*, such as strains of *B. subtilis*, *B. licheniformis*, *B. lentus*, *B. brevis*, *B. stearothermophilus*, *B. alkalophilus*, *B. amyloliquefaciens*, *B. coagulans*, *B. circulans*, *B. lautus*, *B. megaterium* or *B. thuringiensis*, or strains of *Streptomyces*, such as *S. lividans* or *S. murinus*, or gram-negative bacteria such as *Escherichia coli*.

The transformation of the bacteria may be effected by protoplast transformation, electroporation, conjugation, or by using competent cells in a manner known per se (cf. Sambrook et al., supra).

When expressing the enzyme in bacteria such as *E. coli*, the enzyme may be retained in the cytoplasm, typically as insoluble granules (known as inclusion bodies), or may be directed to the periplasmic space by a bacterial secretion sequence. In the former case, the cells are lysed and the granules are recovered and denatured after which the enzyme is refolded by diluting the denaturing agent. In the latter case, the enzyme may be recovered from the periplasmic space by disrupting the cells, e.g., by sonication or osmotic shock, to release the contents of the periplasmic space and recovering the enzyme.

When expressing the enzyme in gram-positive bacteria such as *Bacillus* or *Streptomyces* strains, the enzyme may be retained in the cytoplasm, or may be directed to the extracellular medium by a bacterial secretion sequence. In the latter case, the enzyme may be recovered from the medium as described below.

Method for Producing a Subtilase Variant

The present invention provides a method of producing an isolated enzyme according to the invention, wherein a suitable host cell, which has been transformed with a DNA sequence encoding the enzyme, is cultured under conditions permitting the production of the enzyme, and the resulting enzyme is recovered from the culture.

When an expression vector comprising a DNA sequence encoding the enzyme is transformed into a heterologous host cell it is possible to enable heterologous recombinant production of the enzyme of the invention. Thereby it is possible to make a highly purified subtilase composition, characterized in being free from homologous impurities.

The medium used to culture the transformed host cells may be any conventional medium suitable for growing the host cells in question. The expressed subtilase may conveniently be secreted into the culture medium and may be recovered there-from by well-known procedures including separating the cells from the medium by centrifugation or filtration, precipitating proteinaceous components of the medium by means of a salt such as ammonium sulfate, followed by chromatographic procedures such as ion exchange chromatography, affinity chromatography, or the like.

Detergent Applications

The enzyme of the invention may be added to and thus become a component of a detergent composition. The detergent composition of the invention may for example be formulated as a hand or machine laundry detergent composition including a laundry additive composition suitable for pretreatment of stained fabrics and a rinse added fabric softener composition, or be formulated as a detergent composition for use in general household hard surface cleaning operations, or be formulated for hand or machine dishwashing operations.

In a specific aspect, the invention provides a detergent additive comprising the enzyme of the invention. The detergent additive as well as the detergent composition may comprise one or more other enzymes such as a protease, a lipase, a cutinase, an amylase, a carbohydrase, a cellulase, a pectinase, a mannanase, an arabinase, a galactanase, a xylanase, an oxidase, e.g., a laccase, and/or a peroxidase.

In general the properties of the chosen enzyme(s) should be compatible with the selected detergent, (i.e., pH-optimum, compatibility with other enzymatic and non-enzymatic ingredients, etc.), and the enzyme(s) should be present in effective amounts.

Proteases: Suitable proteases include those of animal, vegetable or microbial origin. Microbial origin is preferred. Chemically modified or protein engineered mutants are included. The protease may be a serine protease or a metallo protease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g., of porcine or bovine origin) and the *Fusarium* protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 68, 76, 87, 97, 101, 104, 106, 120, 123, 167, 170, 194, 206, 218, 222, 224, 235, 245, 252 and 274. Preferred commercially used protease enzymes include RELASE®, ALCALASE®, SAVINASE®, PRIMASE®, EVERLASE®, ESPERASE®, OVOZYME®, CORONASE®, POLARZYME® and KANNASE® (Novozymes A/S), MAXATASE™, MAXACAL™, MAXAPEM™, PROPERASE™, PURAFECT™, PURAFECT OXP™, FN2™, FN3™, FN4™ and PURAFECT PRIME™ (Genencor International, Inc.), BLAP X and BLAP S (Henkel).

Lipases: Suitable lipases include those of bacterial or fungal origin. Chemically modified or protein engineered mutants are included. Examples of useful lipases include lipases from *Humicola* (synonym *Thermomyces*), e.g., from *H. lanuginosa* (*T. lanuginosus*) as described in EP 258 068 and EP 305 216 or from *H. insolens* as described in WO 96/13580, a *Pseudomonas* lipase, e.g., from *P. alcaligenes* or *P. pseudoalcaligenes* (EP 218 272), *P. cepacia* (EP 331 376), *P. stutzeri* (GB 1,372,034), *P. fluorescens*, *Pseudomonas* sp. strain SD 705 (WO 95/06720 and WO 96/27002), *P. wisconsinensis* (WO 96/12012), a *Bacillus* lipase, e.g., from *B. subtilis* (Dartois et al., 1993, *Biochemica et Biophysica Acta* 1131:253-360), *B. stearothermophilus* (JP 64/744992) or *B. pumilus* (WO 91/16422). Other examples are lipase variants such as those described in WO 92/05249, WO 94/01541, EP 407225, EP 260105, WO 95/35381, WO 96/00292, WO 95/30744, WO 94/25578, WO 95/14783, WO 95/22615, WO 97/04079 and WO 97/07202. Preferred commercially used lipase enzymes include LIPOLASE®, LIPOLASE ULTRA® and LIPEX® (Novozymes A/S).

Amylases: Suitable amylases (alpha and/or beta) include those of bacterial or fungal origin.

Chemically modified or protein engineered mutants are included. Amylases include, for example, α-amylases obtained from *Bacillus*, e.g., a special strain of *B. licheniformis*, described in more detail in GB 1,296,839. Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444. Commercially used amylases are DURAMYL®, TERMAMYL®, STAINZYME®, FUNGAMYL® and BAN® (Novozymes A/S), RAPIDASE™, PURASTAR™ and PURASTAR OXAM™ (from Genencor International Inc.).

Cellulases: Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens*, *Myceliophthora thermophila* and *Fusarium oxysporum* disclosed in U.S. Pat. No. 4,435,307, U.S. Pat. No. 5,648,263, U.S. Pat. No. 5,691,178, U.S. Pat. No. 5,776,757 and WO 89/09259. Especially suitable cellulases are the alkaline or neutral cellulases having colour care and whiteness maintenance benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and PCT/DK98/00299. Commercially used cellulases include RENOZYME®, CELLUZYME®, and CAREZYME® (Novozymes A/S), CLAZINASE™, and PURADEX HA™ (Genencor Int. Inc.), and KAC-500(B)™ (Kao Corporation).

Peroxidases/Oxidases: Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257. Commercially used peroxidases include GUARDZYME™ (Novozymes A/S).

Hemicellulases: Suitable hemicellulases include those of bacterial or fungal origin. Chemically modified or protein engineered mutants are included. Suitable hemicellulases include mannanase, lichenase, xylanase, arabinase, galactanase acetyl xylan esterase, glucorunidase, ferulic acid esterase, coumaric acid esterase and arabinofuranosidase as described in WO 95/35362. Suitable mannanases are described in WO 99/64619.

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated e.g., as a granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethylene glycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the invention may be in any convenient form, e.g., a bar, a tablet, a powder, a granule, a paste, a gel or a liquid. A liquid detergent may be aqueous, typically containing up to 70% water and 0-30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g., SKS-6 from Hoechst). The detergent may comprise one or more polymers. Examples are carboxymethyl-cellulose, poly(vinylpyrrolidone), poly(ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine or nonanoyloxybenzenesulfonate. Alternatively, the bleaching system may comprise peroxyacids of e.g., the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in e.g., WO 92/19709 and WO 92/19708.

The detergent may also contain other conventional detergent ingredients such as e.g., fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

It is at present contemplated that in the detergent compositions any enzyme, in particular the enzyme of the invention, may be added in an amount corresponding to 0.01-100 mg of enzyme protein per liter of wash liquor, preferably 0.05-5 mg of enzyme protein per liter of wash liquor, in particular 0.1-1 mg of enzyme protein per liter of wash liquor.

Variations in local and regional conditions, such as water hardness and wash temperature calls for regional detergent compositions. Detergent Examples 1 and 2 provide ranges for the composition of a typical Latin American detergent and a typical European powder detergent respectively.

Detergent Example 1

Typical Latin American Detergent Composition

| Group | Subname | Content |
|---|---|---|
| Surfactants | | 0-30% |
| | Sulphonates | 0-30% |
| | Sulphates | 0-5% |
| | Soaps | 0-5% |
| | Non-ionics | 0-5% |
| | Cationics | 0-5% |
| | FAGA | 0-5% |
| Bleach | | 0-20% |
| | SPT/SPM | 0-15% |
| | NOBS, TAED | 0-5% |
| Builders | | 0-60% |
| | Phosphates | 0-30% |
| | Zeolite | 0-5% |
| | Na2OSiO2 | 0-10% |
| | Na2CO3 | 0-20% |
| Fillers | | 0-40% |
| | Na2SO4 | 0-40% |
| Others | | up to 100% |
| | Polymers | |
| | Enzymes | |
| | Foam regulators | |
| | Water | |
| | Hydrotropes | |
| | Others | |

Detergent Example 2

Typical European Powder Detergent Composition

| Group | Subname | Content |
|---|---|---|
| Surfactants | | 0-30% |
| | Sulphonates | 0-20% |
| | Sulphates | 0-15% |
| | Soaps | 0-10% |
| | Non-ionics | 0-10% |
| | Cationics | 0-10% |
| | Other | 0-10% |
| Bleach | | 0-30% |
| | SPT/SPM | 0-30% |
| | NOBS + TAED | 0-10% |
| Builders | | 0-60% |
| | Phosphates | 0-40% |
| | Zeolite | 0-40% |
| | Na2OSiO2 | 0-20% |
| | Na2CO3 | 0-20% |
| Fillers | | 0-40% |
| | Na2SO4 | 0-40% |
| | NaCl | 0-40% |

-continued

| Group | Subname | Content |
|---|---|---|
| Others | | up to 100% |
| | Polymers | |
| | Enzymes | |
| | Foam regulators | |
| | Water | |
| | Hydrotropes | |
| | Others | |

OTHER APPLICATIONS

The subtilase variants of the present invention may be used in the processing of food, especially in the field of diary products, such as milk, cream and cheese, but also in the processing of meat and vegetables. The subtilase variants of the present invention may also be used in the processing of feed for cattle, poultry, and pigs and especially for pet food. Further, the subtilase variants of the invention may be used for the treatment of hides. The subtilase variants of the invention may also be used in processes for decontaminating instruments, surfaces, and other materials in hospitals, clinics, and meat processing plants, etc. in order to decompose prions or other infectious agents.

Materials and Methods

Method for Producing a Protease Variant

The present invention provides a method of producing an isolated enzyme according to the invention, wherein a suitable host cell, which has been transformed with a DNA sequence encoding the enzyme, is cultured under conditions permitting the production of the enzyme, and the resulting enzyme is recovered from the culture.

When an expression vector comprising a DNA sequence encoding the enzyme is transformed into a heterologous host cell it is possible to enable heterologous recombinant production of the enzyme of the invention. Thereby it is possible to make a highly purified RP-II protease composition, characterized in being free from homologous impurities.

The medium used to culture the transformed host cells may be any conventional medium suitable for growing the host cells in question. The expressed subtilase variant may conveniently be secreted into the culture medium and may be recovered there-from by well-known procedures including separating the cells from the medium by centrifugation or filtration, precipitating proteinaceous components of the medium by means of a salt such as ammonium sulfate, followed by chromatographic procedures such as ion exchange chromatography, affinity chromatography, or the like.

Proteolytic Activity

Enzyme activity can be measured using the PNA assay using succinyl-alanine-alanine-proline-glutamicacid-paranitroaniline as a substrate. The principle of the PNA assay is described in the Journal of American Oil Chemists Society, Rothgeb, T. M., Goodlander, B. D., Garrison, P. H., and Smith, L. A., (1988).

Textiles

Standard textile pieces are obtained from EMPA St. Gallen, Lerchfeldstrasse 5, CH-9014 St. Gallen, Switzerland or CFT, Center For Testmaterials, Vlaardingen, Netherlands. Especially important are EMPA 116 (cotton textile stained with blood, milk and ink), EMPA 117 (polyester/cotton textile stained with blood, milk and ink), C-03 (cotton textile stained with chocolate milk and soot), C-05 (cotton textile stained with blood, milk and ink) and C-10 (cotton textile stained with milk, oil and pigment).

Wash Conditions

| | Region | | | | |
|---|---|---|---|---|---|
| | Latin America | North America | Europe | Asia excl. Japan | Japan |
| Temperature | 20-25° C. | 20-32° C. | 30-60° C. | 15-30° C. | 15-20° C. |
| Washing time | 14-16 min | 12 min | 20-40 min | 14-20 min | 15 min |
| Water hardness* | 6-12° dH | 6° dH | 15° dH | 14° dH | 3° dH |
| Detergent dosage | 1.5-4 g/l | 1.0-1.5 g/l | 4-10 g/l | 1.5-2.5 g/l | 0.5-0.7 g/l |
| Washing pH | As it is | As it is | As it is | As it is | As it is |

*° dH: adjusted by adding $CaCl_2*2H_2O$, $MgCl_2*6H_2O$ and $NaHCO_3$ to Milli-Q water.

Detergents

The enzymes of the invention may be tested in the detergent formulations disclosed in WO 97/07202 or in the detergent examples above. Further, tests could be done in detergents formulations purchased from wfk testgewebe GmbH (Germany) or similar supplier, or in commercial detergents.

List of test detergents from wfk testgewebe:
IEC 60456 Type A* Base Detergent
IEC 60456 Type B Base Detergent
IEC 60456 Type C Detergent
ECE Reference Detergent with Phosphate (1977)
ECE Reference Detergent without Phosphate (1998)
AHAM Standard Detergent
EU ECOLABEL (detergents) Light Duty Detergent
EU ECOLABEL (detergents) PVP However, also one of the following commercial detergents may be used in the wash assay, e.g., Ariel HDP, P&G, Mexico; Omo Multi Acao HDP, Unilever, Brazil; Breeze HDP, Unilever Thailand; Diao Pai, Nice, China; Tide HDL, P&G, US; Wisk HDL, Unilever, US; TOP HDP, Lion, Japan; Attack HDP, Kao, Japan; Ariel Regular HDP, P&G, Europe; Ariel Compact HDPC, P&G, Europe; Persil Megaperls, Henkel, Germany and Persil, Unilever, UK.

Furthermore, a brand extension or color/compact version for the above specified detergent could be used as well.

If the detergent contains enzymes, the detergent should be in-activated before use in order to eliminate the enzyme activity already present in the detergent. This is done by heating a detergent stock solution to 85° C. in 5 minutes in a micro wave oven. The concentration of the detergent stock solution to be inactivated in the micro wave oven is 4-20 g/l.

Automatic Mechanical Stress Assay

The Automatic Mechanical Stress Assay (AMSA) is described in Example 3 below.

Mini Wash Assay

The milliliter scale wash performance assay is conducted under the following conditions:

| | |
|---|---|
| Detergent | Latin American HDP |
| Detergent dose | 1.5-4 g/l |
| pH | As it is |
| Wash time | 14-16 min. |
| Temperature | 20-25° C. |
| Water hardness | 6-12°dH, adjusted by adding $CaCl_2*2H_2O$, $MgCl_2*6H_2O$ and $NaHCO_3$ to milli-Q water. |
| Enzyme conc. | 5 nM, 10 nM, 30 nM |
| Test system | 125 ml glass beakers. Textile dipped in test solution. Continuously lifted up and down into the detergent solution, 50 times per minute. |
| Test solution volume | 50 ml |

After washing the textile piece is flushed in tap water and air-dried and the remission (R) of the test material is measured at 460 nm using a Zeiss MCS 521 VIS spectrophotometer. The measurements are done according to the manufacturer's protocol.

The performance of the new variants is compared to the performance of Savinase by calculating the relative performance:

$$RP=(R_{variant}-R_{BLANK})/(R_{SAVINASE}-R_{BLANK})$$

A variant is considered to exhibit improved wash performance, if it performs better than the reference in at least one detergent composition.

Example 1

Construction and Expression of Enzyme Variants

Site-Directed Mutagenesis:

Subtilisin 309 (SAVINASE®) site-directed variants of the invention comprising specific insertions/deletions/substitutions are made by traditional cloning of DNA fragments (Sambrook et al., Molecular Cloning: A Laboratory Manual, 2nd Ed., Cold Spring Harbor, 1989) produced by PCR with oligonucleotides containing the desired mutations.

Briefly, plasmid DNA pSX222 (E. coli/B. subtilis shuttle vector including appropriate selection marker, origins of replication for Bacillus and E. coli, digestion sites, etc. disclosed in WO 96/34946) bearing the subtilisin 309 wild-type or a subtilisin 309 variant gene is used as template in the PCR reaction. In a first PCR an oligonucleotide containing the desired mutation (anti-sense) and a suitable opposite oligonucleotide (sense) is used. The resulting DNA fragment is used as a sense oligonucleotide in a second PCR together with a suitable anti-sense oligonucleotide. The resulting DNA fragment is digested with suitable restriction enzymes and ligated into a suitable E. coli/Bacillus shuttle vector (e.g., pSX222) digested with the same enzymes.

The ligation product is transformed into competent E. coli and plated on a solid agar containing an appropriate selection marker. DNA purified from a single colony is sequenced to confirm the designed mutation. Plasmid DNA is isolated from E. coli cells bearing plasmids containing subtilisin 309 genes with the designed mutation and is transformed into a suitable competent B. subtilis strain, i, B. subtilis DN1885: Disclosed in WO 01/16285 (e.g., as described by Dubnau et al., 1971, J. Mol. Biol. 56:209-221) and plated on a solid agar containing an appropriate selection marker.

Plasmid DNA from single Bacillus colonies showing protease activity is isolated and sequenced to confirm the designed mutation. Bacillus colonies bearing plasmid DNA including subtilisin 309 genes with the desired mutations are fermented in baffled shake flasks in a suitable media.

Example 2

Purification and Assessment of Enzyme Concentration

After fermentation purification of subtilisin variants is accomplished using Hydrophobic Charge Induction Chromatography (HCIC) and subsequent vacuum filtration. To capture the enzyme, the HCIC uses a cellulose matrix to which 4-Mercapto-Ethyl-Pyridine (4-MEP) is bound.

Beads of the cellulose matrix sized 80-100 micro-m are mixed with a media containing yeast extract and the transformed B. subtilis capable of secreting the subtilisin variants and incubated at pH 9.5 in Unifilter® microplates. As 4-MEP is hydrophobic at pH>7 and the subtilisin variants are hydrophobic at pH 9.5 a hydrophobic association is made between the secreted enzyme and the 4-MEP on the beads. After incubation the media and cell debris is removed by vacuum filtration while the beads and enzyme are kept on the filter. To elute the enzyme from the beads the pH is now lowered by washing the filter with an elution buffer (pH 5). Hereby the enzymes part from the beads and can be retrieved from the buffer.

The concentration of the purified subtilisin enzyme variants is assessed by active site titration (AST). The purified enzyme is incubated with the high affinity inhibitor Cl-2A at different concentrations to inhibit a varying amount of the active sites. The protease and inhibitor binds to each other at a 1:1 ratio and accordingly the enzyme concentration can be directly related to the concentration of inhibitor, at which all protease is inactive. To measure the residual protease activity, a substrate (0.6 mM Suc-Ala-Ala-Pro-Phe-pNA in Tris/HCl buffer) is added after the incubation with inhibitor and during the following 4 minutes the development of the degradation product pNA (paranitrophenol) is measured periodically at 405 nm on an Elisa Reader. Each of the variants of the invention listed in Table 1 herein was purified according to the above procedure and subsequently the enzyme concentration was determined.

Known concentrations of the variants of Table 1 were tested for wash performance in detergent as described below.

Example 3

Wash Performance of Detergent Composition Comprising Subtilase Variants

The enzyme variants of the present application are tested using the Automatic Mechanical Stress Assay (AMSA). With the AMSA test the wash performance of a large quantity of small volume enzyme-detergent solutions can be examined. The AMSA plate has a number of slots for test solutions and a lid firmly squeezing the textile swatch to be washed against all the slot openings. During the washing time, the plate, test solutions, textile and lid are vigorously shaken to bring the test solution in contact with the textile and apply mechanical stress. For further description see WO 02/42740 especially the paragraph "Special method embodiments" at page 23-24. The assay is conducted under the experimental conditions specified below.

| | |
|---|---|
| Detergent | Latin American type HDP |
| Detergent dosage | 2.2 g/l |
| Test solution volume | 160 micro l |
| pH | Adjusted to pH 9.5-10.5 with NaHCO$_3$. |
| Wash time | 14 minutes |
| Temperature | 20° C. |
| Water hardness | 9° dH* |
| Enzyme concentration in test solution | 5 nM, 10 nM and 30 nM |
| Test material | C-10 |

*° dH: adjusted by adding CaCl$_2$*2H$_2$O; MgCl$_2$*6H$_2$O (Ratio Ca$^{2+}$:Mg$^{2+}$ = 2:1) to milli-Q water.

The Latin American type detergent was composed according to the provisions in Detergent Example 1 herein. After washing the textile pieces are flushed in tap water and air-dried.

The performance of the enzyme variant is measured as the brightness of the colour of the textile samples washed with that specific enzyme variant. Brightness can also be expressed as the intensity of the light reflected from the textile sample when luminated with white light. When the textile is stained the intensity of the reflected light is lower, than that of a clean textile. Therefore the intensity of the reflected light can be used to measure wash performance of an enzyme variant.

Color measurements are made with a professional flatbed scanner (PFU DL2400pro), which is used to capture an image of the washed textile samples. The scans are made with a resolution of 200 dpi and with an output colour dept of 24 bits. In order to get accurate results, the scanner is frequently calibrated with a Kodak reflective 1T8 target. To extract a value for the light intensity from the scanned images, a special designed software application is used (Novozymes Color Vector Analyzer). The program retrieves the 24 bit pixel values from the image and converts them into values for red (r), green (g) and blue (b). The intensity value (Int) is calculated by adding the (r), (g) and (b) values together as vectors and then taking the length of the resulting vector:

$$Int = \sqrt{r^2 + g^2 + b^2}.$$

The wash performance (P) of a variant is defined as the light intensity value of textile surface washed with enzyme variant:

$$P = Int(v)$$

The results are presented in Table 2 where the performance is given as relative performance of a new variant versus the performance of Savinase at 10 nM protease concentration:

$$RP \text{ is } (P_{VARIANT} - P_{BLANK})/(P_{SAVINASE} - P_{BLANK})$$

TABLE 2

Wash performance test results with subtilase variants relative to the performance of Savinase.

| Mutations in variant | Relative performance |
| --- | --- |
| T143K, Y167A, R170S, A194P | 1.8 |
| Y167A, R170S, A194P, K251R | 1.6 |
| Y167A, R170S, A194P, S265K | 2.0 |
| Y167A, R170S, A194P, V244R | 1.9 |
| S141E, Y167A, R170S, A194P | 1.1 |
| Y167A, R170S, M175I | 1.2 |
| Y167A, R170S, A172T | 1.2 |
| Y167A, R170S, A174V, M175F | 1.4 |
| Y167A, R170S, A172V, A174V | 1.5 |
| Y167A, R170S, A172E | 1.3 |
| Y167A, R170S, M175L | 1.5 |
| Y167A, R170S, A174T | 1.2 |
| Y167A, R170S, A174T, M175L | 1.4 |
| G53C, G61E | 1.3 |
| A98S, S99D, G100S | 1.4 |
| S9R, T22A, V68A, S99A, *99aD | 1.7 |
| S9R, P14H, R19L, N62D | 1.8 |
| G61P, *99aS | 1.7 |
| N43S, N62D | 1.7 |
| *96aG, P131S, V203A, A228T | 1.8 |
| N62D, A232C, Q236L, Q245N | 2.0 |
| *96aA, A98T, R247K | 2.0 |
| S99D, S101R, S103A, V104I, G160S, A194P, L217D | 1.4 |
| *61aD | 1.3 |
| N62D, S106A | 2.2 |
| V68A, S106M, N184D | 1.6 |
| S9R, A15T, *97aV, H120N | 1.4 |
| A15M, A16P, *99aD | 1.6 |
| *99aE, G160S, S163T, G195S, G211S, K237R, G258A, T260L | 1.2 |
| G23S, *99aD, A194P, S242T, Q245R | 1.5 |
| G100S, N173D | 1.4 |
| Y167A, R170S, A172E | 1.1 |

TABLE 2-continued

Wash performance test results with subtilase variants relative to the performance of Savinase.

| Mutations in variant | Relative performance |
| --- | --- |
| A98T, Q137L, Y167A, R170S, M175L | 1.1 |
| *98aA, S99D | 1.8 |
| S99A, *99aD, V203A | 1.8 |
| N62D, K237R | 2.1 |
| V11M, N76D, L126F, K251R | 1.4 |
| S9F, A15L, A16P, T22I, *98aA, S99D, R170H | 1.2 |
| *96aA, *130aG, P131H | 1.5 |
| E54D, N62D | 2.0 |
| *98aA, *98bS, S99G, S101T | 1.8 |
| S9R, A15T, V68A, I79T, G102S, P131H, Q137H | 1.7 |
| *100aA, *100bG, *100cS, *100dG | 1.7 |
| V68A, L111I | 1.8 |
| *98aA, R170H, Q245R | 1.8 |
| I35V, N62D, N183D, T224S | 1.2 |
| *97aG, P131S, V203A, A228T | 1.4 |
| S9R, R10K, P14Q, T22A, Y167A, R170S | 1.6 |
| S9R, *22aL, S57A, G61E, *98aA, V139L, N173S | 1.3 |
| P14T, N18K, Y167A, R170S | 2.0 |
| S9R, Q12E, P14Q, K27R, Y167A, R170S | 1.7 |
| N62D, R170L | 1.7 |
| N62D, R170S, Q245R | 1.4 |
| Y167A, R170S, A194P, K251R, S265K | 2.0 |
| P14T, N18K, Y167A, R170S, A194P | 2.0 |
| N62D, A151G, K237R | 2.0 |
| N62D, A151G, Q245R | 1.9 |
| N62D, A151G, K237R, Q245R | 2.0 |

Example 4

Wash Performance of Detergent Composition Comprising Subtilase Variants

The milliliter scale wash performance assay was conducted under the following conditions:
Mini Wash Assay

| | |
| --- | --- |
| Detergent | Persil, Lever, UK, HDP |
| Detergent dose | 6 g/l |
| pH | As it is |
| Wash time | 20 min. |
| Temperature | 30° C. |
| Water hardness | 15° dH, adjusted by adding $CaCl_2 \cdot 2H_2O$, $MgCl_2 \cdot 6H_2O$ and $NaHCO_3$ (4:1:7.5) to milli-Q water. |
| Enzyme conc. | 2.5 nM, 5 nM, 10 nM, 30 nM, 60 nM |
| Test system | 125 ml glass beakers. Textile dipped in test solution. Continuously lifted up and down into the detergent solution, 50 times per minute. Swatch used: EMPA 116 (2.5 cm × 7 cm) |
| Test solution volume | 50 ml |

After washing the textile piece is flushed in tap water and air-dried and the remission (R) of the test material is measured at 460 nm using a Zeiss MCS 521 VIS spectrophotometer. The measurements are done according to the manufacturer's protocol.

The performance of the new variants is compared to the performance of Savinase at 10 nM protease concentration by calculating the relative performance:

$$RP = (R_{variant} - R_{BLANK})/(R_{SAVINASE} - R_{BLANK})$$

A variant is considered to exhibit improved wash performance, if it performs better than the reference in at least one detergent composition.

Scoring: A score=1 is given for variants with an improved wash performance equal to or better than 1.1.

| Mutations | Score |
|---|---|
| S103A, V104I, G159D, A232V, Q236H, Q245R | 1 |
| S9R, A15T, T22A, V139L | 1 |
| S9R, A15T, G61E, A85T, E89Q, P239L, Q245C | 1 |
| S9R, A15T, V68A, H120N, Q245R | 1 |
| N248R | 1 |
| S9R, A15T, *22aL, V139L, N204D, Q245L | 1 |
| N218S | 1 |
| S9R, A15T, V68A, Q245R, N252K | 1 |
| S9R, A15T, V68A, Q245R, H120N | 1 |
| V68A, S106A, H120N | 1 |
| V68A, S106A, N252K | 1 |
| A15T, V68A, S99G, Q245R, N261D | 1 |
| S9R, V68A, S99G, Q245R, N261D | 1 |
| V68A, S99G, Q245R, N261D | 1 |
| S9R, A15T, V68A, S99G, N261D | 1 |
| S9R, A15T, V68A, Q245R, N261D | 1 |
| S9R, A15T, *22aL, V139L, S163G, N204D, Q245L | 1 |
| Q245R, N252H | 1 |
| S9R, *22aL, G61E, *97aA, M119I, Q137H, N173S | 1 |
| V68A, S106A, T213A | 1 |
| S9R, A15T, V68A, H120N, P131S, Q137H, Q245M | 1 |
| S9R, A15T, V68A, I72F, S99G, Q245R, N261D | 1 |
| S9R, A15T, V68A, S99D, Q245R, N261D | 1 |
| S9R, A15T, V68A, S99G, A194P, Q245R, N261D | 1 |
| S9R, A15T, V68A, N76I, S99G, Q245R, N261D | 1 |
| S9R, A15T, V68A, S99G, A228V, Q245R, N261D | 1 |

The invention claimed is:

1. A variant of a subtilisin 309 comprising the following set of modifications:

S9R, A15T, V68A, S99G, A228V, Q245R, N261D; wherein the variant has protease activity and each position corresponds to a position of the amino acid sequence of SEQ ID NO: 1.

2. The variant of claim 1, which further comprises one or more of the modifications K27R, *36D, S56P, N62D, N76D, S87N, G97N, S101G, S101R, S103A, V104A, V104I, V104N, V104Y, S106A, H120D, H120N, N123S, G159D, Y167A, R170S, R170L, A194P, N204D, V205I, Q206E, L217D, N218S, N218D, M222S, M222A, T224S, A232V, K235L, Q236H, N248D, N252K, T274A, S101G+V104N, S87N+S101G+V104N, K27R+V104Y+N123S+T274A, and N76D+S103A+V104I.

3. A cleaning or detergent composition, comprising a variant of claim 1 and a surfactant.

4. The composition of claim 3, which additionally comprises a cellulase, a lipase, an amylase, a cutinase, a protease, a hemicellulase, an esterase, a lactase, a glycoamylase, a polygalacturonase, a beta-galactosidase, a ligninase, or a mixture thereof.

5. An isolated DNA sequence encoding a subtilase variant of claim 1.

6. An expression vector comprising the isolated DNA sequence of claim 5.

7. A microbial host cell transformed with the expression vector of claim 6.

8. The microbial host cell of claim 7, which is a bacterium.

9. A method for producing a subtilase variant, comprising
   (a) culturing a host cell of claim 7 under conditions conducive to the expression and secretion of the variant, and
   (b) recovering the variant.

* * * * *

SEQUENCE LISTING

<160> NUMBER OF SEQ ID NOS: 2

<210> SEQ ID NO 1
<211> LENGTH: 275
<212> TYPE: PRT
<213> ORGANISM: B. amyloliquefaciens (subtilisin BPN')

<400> SEQUENCE: 1

Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Ser His
    50                  55                  60

Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
        115                 120                 125

Pro Ser Gly Ser Ala Ala Leu Lys Ala Ala Val Asp Lys Ala Val Ala
    130                 135                 140

Ser Gly Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Tyr Asn Gly Thr Ser Met Ala Ser
    210                 215                 220

Pro His Val Ala Gly Ala Ala Leu Ile Leu Ser Lys His Pro Asn
225                 230                 235                 240

Trp Thr Asn Thr Gln Val Arg Ser Ser Leu Glu Asn Thr Thr Lys
                245                 250                 255

```
-continued

Leu Gly Asp Ser Phe Tyr Tyr Gly Lys Gly Leu Ile Asn Val Gln Ala
            260                 265                 270

Ala Ala Gln
        275

<210> SEQ ID NO 2
<211> LENGTH: 269
<212> TYPE: PRT
<213> ORGANISM: B. lentus (subtilisin 309)

<400> SEQUENCE: 2

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```